United States Patent [19]

Ozaki et al.

[11] Patent Number: 5,518,902
[45] Date of Patent: May 21, 1996

[54] HIGH PULLULAN CONTENT PRODUCT, AND ITS PREPARATION AND USES

[75] Inventors: Yoshihide Ozaki; Tatsuo Nomura; Toshio Miyake, all of Okayama, Japan

[73] Assignee: Kabushiki Kaisha Hayashibara Seibutsu Kagaku Kenkyujo, Okayama, Japan

[21] Appl. No.: 361,548

[22] Filed: Dec. 22, 1994

Related U.S. Application Data

[62] Division of Ser. No. 57,908, May 7, 1993, abandoned.

[30] Foreign Application Priority Data

Aug. 20, 1992 [JP] Japan .................................. 4-265285

[51] Int. Cl.⁶ .............................. C12P 19/10; C12P 19/04
[52] U.S. Cl. ...................... 435/102; 435/101; 536/123.12
[58] Field of Search ....................... 536/123.12; 435/101, 435/102

[56] References Cited

U.S. PATENT DOCUMENTS

| | | | |
|---|---|---|---|
| 3,912,591 | 10/1975 | Kato et al. | 435/102 |
| 4,579,259 | 4/1986 | Hirao et al. | 222/389 |
| 4,623,394 | 11/1986 | Nakamura et al. | 106/122 |
| 4,628,028 | 12/1986 | Katkocin et al. | 435/102 |
| 4,927,636 | 5/1990 | Hijiya et al. | 424/409 |
| 5,268,460 | 12/1993 | Thorne et al. | 536/1.11 |

FOREIGN PATENT DOCUMENTS

| | | |
|---|---|---|
| 0382355 | 12/1989 | European Pat. Off. . |
| 2199553 | 12/1974 | France . |
| 49-42894 | 4/1974 | Japan . |
| 50-64441 | 5/1975 | Japan . |
| 116545 | 9/1975 | Japan . |
| 51-543 | 5/1976 | Japan . |
| 100470 | 9/1976 | Japan . |
| 119321 | 10/1976 | Japan . |
| 41252 | 3/1977 | Japan . |
| 56603 | 5/1977 | Japan . |
| 130993 | 11/1977 | Japan . |
| 53-12417 | 2/1978 | Japan . |
| 19416 | 2/1978 | Japan . |
| 53-54593 | 5/1978 | Japan . |
| 53-79045 | 7/1978 | Japan . |
| 119741 | 10/1978 | Japan . |
| 108828 | 8/1979 | Japan . |
| 57-67602 | 4/1982 | Japan . |
| 213076 | 12/1983 | Japan . |
| 219238 | 11/1985 | Japan . |
| 28369 | 2/1988 | Japan . |
| 122739 | 5/1988 | Japan . |
| 289520 | 11/1990 | Japan . |
| 57141401 | 9/1992 | Japan . |

OTHER PUBLICATIONS

McNeil et al, Biotechnology and Bioengineering 33:1210–1212 (1989).
Chemical Abstracts 117(15):149331a (1992).
McNeil et al; "Temperature effects on polysaccharide formation by Aureobasidium pullulans in stirred tanks" pp. 521–526; Enzyme Microb. Technol., 1990, vol. 12, Jul.
Boa et al; "Pullulan from Peat Hydrolyzate Fermentation Kinetics"; pp. 463–470; Biotechnology and Bioengineering, vol. XXX (1987).
Bulmer et al; "The effect of ammonium ions and pH on the elaboration of the fungal extracellular polysaccharide, pullulan, by *Aureobasidium pullulans*"; pp. 362–365; Appl. Microbiol Biotechnol (1987).

*Primary Examiner*—Michael G. Wityshyn
*Assistant Examiner*—Francisco C. Prats
*Attorney, Agent, or Firm*—Browdy and Neimark

[57] ABSTRACT

Disclosed is a novel high pullulan content product containing pullulan having an average molecular weight less than 250,000, said product being prepared by continuously cultivating a microorganism capable of producing pullulan in a nutrient culture medium containing a 10–20 w/v % saccharide while controlling the viscosity of the nutrient culture medium to a level below 30 cp. The product can be advantageously used in a variety of fields such as viscosity-imparting agent, coating agent, adhesive, formed product, food product, cosmetic, pharmaceutical, and material for agriculture, forestry, stock raising and paper processings, as well as for mining and manufacturing industries.

12 Claims, No Drawings

HIGH PULLULAN CONTENT PRODUCT, AND ITS PREPARATION AND USES

This is division of application Ser. No. 08/057,908 filed May 7, 1993, now abandoned.

BACKGROUND OF THE INVENTION

1. Field of the Invention

The present invention relates to a high pullulan content product, and its preparation and uses; more particularly, to a high pullulan content product containing pullulan having an average molecular weight less than 250,000, said product being prepared by allowing a microorganism capable of producing pullulan to continuously cultivate in a nutrient culture medium containing a 10–20 w/v % saccharide while controlling the viscosity of said nutrient culture medium to a level below 30 centipoise (the wording "centipoise" will be abbreviated as "cp" hereinafter), as well as to the preparation and uses of said product.

2. Description of the Prior Art

Pullulan, a viscous glucan which is prepared by allowing a microorganism capable of producing pullulan to cultivate under aerobic conditions in a nutrient culture medium containing a saccharide such as mono- and oligo-saccharides, has been industrially produced.

Examples of such a preparation of pullulan which have been proposed are a method as disclosed in Japanese Patent Laid-Open No.42,894/74 wherein proposed is a method to increase the pullulan productivity by adjusting the initial pH of a nutrient culture medium to pH 5.5–8.0, preferably, to a relatively-high level of pH; and a method as disclosed in Japanese Patent Laid-Open No.130,993/77 wherein proposed is a method to increase the pullulan productivity by culturing a microorganism capable of producing pullulan while preventing the decrease of the viscosity of a nutrient culture medium by coexisting an amylase-inhibitory substance. It was found that these methods, however, are batchwise cultures so that they are not necessarily satisfiable in view of the industrial-scale production of pullulan.

The following publications disclose a preparation of pullulan prepared by a continuous culture of a microorganism capable of producing pullulan:

(1) *Applied Microbiology and Biotechnology*, Bulmer et at., Vol.25, pp.362–365 (1987);

(2) *Biotechnology and Bioengineering*, Boa et al., Vol.30, pp.463–470 (1987);

(3) *Biotechnology and Bioengineering*, McNeil et al., Vol.33, pp.1210–1212 (1989); and (4) *Enzyme and Microbial Technology*, McNeil et al., Vol.12, pp.521–526 (1990).

Preparations of pullulan by using a continuous culture, however, were biochemically and biotechnologically studied in these publications, the concentration of a saccharide such as glucose, sucrose and peat hydrolyzate was low as 2–5 w/v %, and the influence of the viscosity of a nutrient culture medium was not studied. Boa et al. did not clearly refer to the pH of a nutrient culture medium, while Bulmer et al. effected a continuous culture at pH 5.5, and McNeil et al. reported that the optimum pH of a pullulan-producing microorganism was pH 4.5. Among these continuous cultures, the maximum pullulan productivity per L and per an hour ($gL^{-1}h^{-1}$) (hereinafter will be referred to as "pullulan productivity") was low as 0.48 as disclosed in the publication of Boa et al., and the cultivation periods of the continuous cultures are not clear. Accordingly, in accordance with these publications it seems to be substantially difficult to produce a high pullulan content product which is advantageously useful in an industrial-scale production.

It has been a great demand to overcome the drawbacks of the above conventional methods and to establish a high pullulan content product which is prepared by a novel and industrially advantageous continuous-culture, as well as to establish its uses.

SUMMARY OF THE INVENTION

The present inventors have studied a preparation of a high pullulan content product by using a continuous culture, more particularly, we studied a high pullulan content product which is advantageously useful in an industrial-scale production, as well as its preparation and uses, by investigating the influence of the viscosity of a nutrient culture medium, which contains a relatively-high concentration of a saccharide, on the pullulan productivity.

As a result, we found that unlike conventional techniques (i) a preparation, which comprises a step of allowing a microorganism capable of producing pullulan to continuously cultivate in a nutrient culture medium containing a 10–20 w/v % saccharide while controlling the viscosity of said nutrient culture medium to a level below 30 cp, produces a high pullulan content product containing pullulan having an average molecular weight less than 250,000 in a relatively-high pullulan productivity; (ii) the continuous culture is stably effective for a relatively-long period of time; and (iii) the preparation is advantageously useful as an industrial-scale production. Accordingly, we accomplished such a preparation of a high pullulan content product and its uses in a variety of fields such as food products, cosmetics, pharmaceuticals, and materials for agriculture, forestry, fishery and paper processing, as well as for mining and manufacturing industries. Thus, we accomplished this invention.

DETAILED DESCRIPTION OF THE INVENTION

The present invention relates to a high pullulan content product, and its preparation and uses.

Any microorganism of any strain can be used in the invention as long as it can produce pullulan. For example, strains of microorganisms of the genus Aureobasidium such as *Aureobasidium fermentans* var *fermentans* IFO 6410, *Aureobasidium fermentans* var *fusca* IFO 6402, *Aureobasidium pullulans* IFO 6353 and *Aureobasidium pullulans* IFO 4464, as well as their mutants, can be suitably used.

The nutrient culture media for cultivating the microorganisms usable in the invention include those which contain adequate amounts of carbon resources, nitrogen resources, organic nutrient-resources and inorganic materials. Usually, one or more saccharides selected from glucose, maltose, maltooligosaccharides, isomaltooligosaccharides, starch syrup or starch hydrolysates, sucrose, fructose, saccharified starch, invert sugars, isomerized sugars and molasses are used as a carbon source in a concentration in the range of 10–20 w/v %, preferably, 10–18 w/v %. One or more substances selected from inorganic nitrogen-resources such as an ammonium salt and nitrate; and organic nitrogen-resources such as a glutamate, peptone, yeast extract and corn steep liquor are used as a nitrogen resource. Phosphates, magnesium salts, ferric salts and ferrous salts can be suitably used as an inorganic substance.

The continuous cultures usable in the invention are effected under aerobic conditions while controlling the viscosity of a nutrient culture medium to a level below 30 cp. Preferably, the pH and temperature conditions are a pH of 4.0 or lower, more preferably, a pH exceeding 2.0 but not higher than 4.0, and a temperature in the range of about 25°–30° C.

The methods to control the viscosity of a nutrient culture medium to a level below 30 cp usable in the invention are effected, for example, by intermittently or continuously replacing a part of the nutrient culture medium with a supplemental nutrient-culture-medium while controlling the dilution speed of the nutrient culture medium at about $0.01-0.1h^{-1}$ by regulating the feeding speed of the nutrient culture medium; or by adding to the nutrient culture medium with an adequate amount of an enzyme or amylase such as a liquefying α-amylase and isoamylase which partially hydrolyze pullulan to lower the viscosity of the nutrient culture medium. If necessary, a precultivated nutrient-culture-medium can be advantageously used as a supplemental nutrient-culture-medium.

The high pullulan content culture thus obtained is in usual manner sterilized and concentrated, and, if necessary further decolored and desalted to obtain a high pullulan content product in the form of liquid. If necessary, the resultant product is pulverized, followed by recovering the pulverized high pullulan content product. The high pullulan content products thus obtained contain pullulan having an average molecular weight less than 300,000, preferably, about 40,000–250,000 in an amount of about 50 w/w %, based on the weight of the dry solid (d.s.b.) or higher, preferably, about 55–90 w/w %, d.s.b. The products can be suitably prepared into a more high-purity pullulan product by using molecular-weight fractionation, as well as sedimentation and separation using an organic solvent, if necessary.

The present high pullulan content product has a satisfiable water-solubility, viscosity-imparting ability, film-forming ability, transparence, gas-barrier ability, oil tolerance, salt tolerance, adhesiveness, forming ability, edibility and substantial no assimilability, and these render it advantageously useful in a viscosity-imparting agent, coating agent, adhesive and formed product.

The present high pullulan content product is widely used in a variety of industrial fields, for example, food products such as a growth-promoting agent for microorganisms of Bifidobacterium, food of dietary fiber, and low-caloric food; cosmetics such as a dentifrice, milky lotion, cream, pack, hair tonic, hair lotion, hair cream, shampoo and bath salts; pharmaceuticals such as an ointment, tablet, capsule and plasma expander; materials for agriculture, forestry, fishery and stock raising such as a coating seed, granulated agricultural chemical, formed fertilizers and formed feed and pet food; materials for paper processings such as a binder and sizing; and materials for mining and manufacturing industries such as an agent for treating wastewater, welding rod and molding.

When the present high pullulan content product is used in the above-mentioned products, it can be advantageously incorporated therein alone or in combination with a polyhydric alcohol such as glycerine, sorbitol, maltitol and lactitol to meet to their final use.

If necessary, the present high pullulan content product can be suitably incorporated in the above-mentioned products together with one or more substances selected from polysaccharides excluding pullulan, plastic materials, fillers, adjuvants, excipients, viscosity-imparting agents, surface active agents, foaming agents, antifoaming agents, pH-regulatory agents, stabilizers, flame retarders, mold releases, antiseptics, coloring agents, flavor-imparting agents, nutrient substances, cigarettes, tobaccos, taste-imparting agents, therapeutic agents and biologically active agents. The wording "to incorporate the present high pullulan content product in a product" as referred to in the invention means a process to incorporate the high pullulan content product in a material before completion of its processing. For example, conventional methods such as mixing, kneading, soaking, applying, spreading, spraying and injecting can be suitably chosen.

In case of preparing a viscosity-imparting agent, the methods as disclosed in Japanese Patent Laid-Open Nos.51, 543/76, 41,252/77 and 213,076/83 can be employed. In case of preparing a coating agent, the methods as disclosed in Japanese Patent Laid-Open Nos.56,603/77, 19,416/78 and 119,741/78 can be employed. In case of preparing an adhesive, the methods as disclosed in Japanese Patent Laid-Open Nos.119,321/76, 54,593/78 and 108,828/79 can be employed. In case of preparing a formed product, the methods as disclosed in Japanese Patent Laid-Open Nos.116,545/75, 4,272/76 and 100,470/76 can be employed. In case of preparing a food product, the methods as disclosed in Japanese Patent Laid-Open Nos.79,045/78, 219,238/85 and 289,520/90 can be employed. In case of preparing a cosmetic, the methods as disclosed in Japanese Patent Laid-Open Nos.64,441/75 and 28,369/88 can be employed. In case of preparing a pharmaceutical, the methods as disclosed in Japanese Patent Laid-Open Nos.12,417/78, 67,602/82 and 122,739/88 can be employed.

The following experiments will explain the preparation of the high pullulan content product by the continuous culture according to the present invention.

Experiment 1

Influence of concentration of saccharide and control of viscosity on pullulan productivity Experiment 1-A Viscosity control by the feeding of nutrient culture medium A nutrient culture medium as shown in. Table 1 was placed in a jar fermentor, autoclaved at 120° C. for 20 minutes in usual manner, and cooled to about 27° C. A seed culture of a microorganism was aseptically inoculated in the autoclaved nutrient culture medium and cultured under aerobic conditions while stirring and keeping the pH at 3.6–3.8 by the addition of hydrochloric acid or sodium hydroxide.

The seed culture was prepared by cultivating a microorganism of the species *Aureobasidium pullulans* IFO 6353 in the same nutrient culture medium at about 27° C. for 24 hours.

TABLE 1

| Components of nutrient culture medium | Concentration (w/v %) |
| --- | --- |
| Saccharides (a starch syrup saccharified with an acid, a dextrose equivalent (DE) of 43) | 8–25 |
| Peptone | 0.2 |
| $K_2HPO_4$ | 0.2 |
| NaCl | 0.2 |
| $MgSO_4 \cdot 7H_2O$ | 0.04 |
| $FeSO_4 \cdot 7H_2O$ | 0.001 |

The method for controlling the viscosity of a nutrient culture medium was effected by regulating the dilution rate of a supplemental nutrient-culture-medium in a manner that a part of the nutrient culture medium was intermittently or continuously replaced with the supplemental nutrient-culture-medium. The feeding of the supplemental nutrient-culture-medium was started after the culture reached to a stationary state. The viscosity of the nutrient culture medium was determined by sampling a portion of the nutrient culture medium during the continuous culture, removing microorganisms from the sample, and determining the viscosity of the resultant sample with an E-type rotational viscometer at 30° C. The pullulan productivity was determined by measuring the pullulan content (g), d.s.b., per L and per an hour in a portion of a nutrient culture medium sampled at a time of 300–320 hours during the continuous culture. The wording "the pullulan content" as mentioned above means the amount of a relatively-high molecular weight substance which does not dissolve in 75 v/v % methanol and mainly forms maltotriose when hydrolyzed by pullulanase (EC 3.2.1.41).

As a control, the same continuous culture was carried out without controlling the viscosity of a nutrient culture medium, i.e. without feeding thereto a supplemental nutrient-culture-medium.

The results were as shown in Table 2.

viscosities of the nutrient culture media are kept to a level below 30 cp.

Experiment 1-B

Viscosity control in the coexistence of isoamylase

A continuous culture was effected by using a nutrient culture medium consisting of the same compositions as in Experiment 1-A, feeding the nutrient culture medium a supplemental nutrient-culture-medium in order to control the viscosity of the nutrient culture medium to a level of 60 cp or higher but below 90 cp while replacing a part of the nutrient culture medium with the supplemental nutrient-culture-medium, and further adding to the nutrient culture medium an isoamylase specimen commercialized by Hayashibara Biochemical Laboratories Inc., Okayama, Japan, to keep the viscosity of the nutrient culture medium within the viscosity ranges as shown in Table 3. Other conditions were the same as in Experiment 1-A.

The results were as shown in Table 3.

TABLE 2

| Culture conditions | | Pullulan productivity ($gL^{-1}h^{-1}$) | | | | |
|---|---|---|---|---|---|---|
| Feeding of supplemental | | Saccharide concentration (w/v %) | | | | |
| nutrient-culture-medium | Viscosity control | 8 | 10 | 16 | 18 | 20 |
| No | Uncontrolled (90 cp or higher) | 0.52 | 0.54 | 0.53 | 0.51 | 0.48 |
| Yes | Controlled at 60 cp or higher but below 90 cp | 0.60 | 0.66 | 0.66 | 0.62 | 0.60 |
| Yes | Controlled at 30 cp or higher but below 60 cp | 0.71 | 0.78 | 0.78 | 0.78 | 0.77 |
| Yes | Controlled to a level below 30 cp | 0.78 | 0.89 | 0.91 | 0.89 | 0.88 |

Note: In the table, the symbol "cp" means centipoise.

As evident from the results in Table 2, it was revealed that, in continuous cultures wherein nutrient culture media containing different concentrations of saccharides are used and the viscosities of the nutrient culture media are controlled by

TABLE 3

| Culture conditions | | Pullulan productivity ($gL^{-1}h^{-1}$) Saccharide concentration (w/v %) | | | | |
|---|---|---|---|---|---|---|
| Coexistence of isoamylase | Viscosity control | 8 | 10 | 16 | 18 | 20 |
| No | Controlled at 60 cp or higher but below 90 cp | 0.56 | 0.62 | 0.60 | 0.56 | 0.54 |
| Yes | Controlled at 30 cp or higher but below 60 cp | 0.70 | 0.80 | 0.81 | 0.80 | 0.78 |
| Yes | Controlled to a level below 30 cp | 0.80 | 0.94 | 1.01 | 0.97 | 0.92 |

Note: In the table, the symbol "cp" means centipoise.

replacing a part of the nutrient culture media with a supplemental nutrient-culture-medium, a high-level of pullulan productivity of $0.88 gL^{-1}h^{-1}$ or higher, d.s.b., is attained when the concentration of saccharides is kept to a level in the range of 10–20 w/v %, preferably, 10–18 w/v %, and the As evident from the results in table 3, it was revealed that, in continuous cultures wherein the viscosities of nutrient culture media are controlled by the addition of isoamylase, a high-level of pullulan productivity of $0.92 gL^{-1}h^{-1}$ or higher, d.s.b., is attained when the concentration of a saccharide is kept to a level in the range of 10–20 w/v %, preferably, 10–18 w/v %, and the viscosities of the nutrient culture media are kept to a level below 30 cp.

Experiment 2

Influence of pH control on pullulan productivity in viscosity-controlled continuous culture The pullulan productivity was studied by conducting a continuous culture by using a nutrient culture medium containing 16 w/v % of a saccharide, and, similarly as in Experiment 1-B, keeping the viscosity of the nutrient culture medium in the coexistence of isoamylase at a level below 30 cp and at different pHs.

The results were as shown in Table 4.

TABLE 4

| pH | Pullulan productivity ($gL^{-1}h^{-1}$) |
|---|---|
| 2.2 | 0.92 |
| 2.5 | 0.94 |
| 3.0 | 0.98 |
| 3.5 | 0.95 |
| 3.8 | 0.93 |
| 4.0 | 0.92 |
| 4.5 | 0.84 |
| 5.0 | 0.81 |

As evident from the results in Table 4, it was revealed that an extremely-high level of pullulan productivity of $0.92gL^{-1}h^{-1}$ or higher, d.s.b., is attained when the pH is controlled to a pH of 4.0 or lower, preferably, to a pH-level exceeding 2.0 but not higher than 4.0.

The preparation of the present high pullulan content product and its uses will be explained in Examples A and B respectively.

EXAMPLE A-1

High pullulan content product

A seed culture of a microorganism of the species *Aureobasidium pullulans* IFO 6353 was inoculated and continuously cultivated in a nutrient culture medium consisting of the same components as shown in Table 1 except that a 14 w/v % solution of "SUN ROSE®", a starch syrup having a relatively-high DE commercialized by Hayashibara Shoji, Inc., Okayama, Japan, was used as a saccharide. The continuous culture was carried out at 27° C. for one month while controlling the pH in the range of 3.6–3.8 and replacing a part of the nutrient culture medium with a supplemental nutrient-culture-medium at a dilution rate of $0.01–0.04h^{-1}$ in order to control the viscosity of the nutrient culture medium to a level below 30 cp. The nutrient culture medium 4 days after the initiation of the continuous culture was recovered, and in usual manner membrane-filtered, decolored, concentrated and dried to obtain a high pullulan content product in the form of powder.

The analytical results were as shown in Table 5.

TABLE 5

| Items | Composition (w/w %, d.s.b. in a final product) |
|---|---|
| Water content | 4.6 |
| Ash | 2.5 |
| Pullulan | 60.3 |
| Residual saccharides | 32.5 |
| Crude proteins | 0.1 |
| Average molecular weight | 62,000 |

The product can be advantageously used in a viscosity-imparting agent, coating agent, adhesive, formed product, food product, chemical, pharmaceutical and material for agriculture, forestry, fishery and paper processings, as well as for mining and manufacturing industries.

EXAMPLE A-2

High pullulan content product

A seed culture of a microorganism of the species *Aureobasidium pullulans* IFO 6353 was inoculated and continuously cultivated in a nutrient culture medium consisting of the same components as in Example A-1. The continuous culture was carried out at 27° C. for 2 months while replacing a part of the nutrient culture medium at a dilution rate of $0.01–0.02h^{-1}$ with a supplemental nutrient-culture-medium added with or without "Hi-Maltosin S", a liquefying α-amylase commercialized by Ueda Chemical Co., Ltd., Osaka, Japan, in order to control the viscosity of the nutrient culture medium to a level below 30 cp and the pH of the nutrient culture medium to 3.2–3.4. Similarly as in Example A-1, the resultant nutrient culture medium was recovered and treated to obtain a high pullulan content product in the from of powder. The results were as shown in Table 6.

TABLE 6

| Items | Composition (w/w %, d.s.b. in a final product) |
|---|---|
| Water content | 5.2 |
| Ash | 3.1 |
| Pullulan | 71.4 |
| Residual saccharides | 20.2 |
| Crude proteins | 0.1 |
| Average molecular weight | 41,000 |

The product can be advantageously used in a viscosity-imparting agent, coating agent, adhesive, formed product, food product, chemical, pharmaceutical and material for agriculture, forestry, fishery and paper processings, as well as for mining and manufacturing industries.

EXAMPLE A-3

High pullulan content product

A seed culture of a microorganism of the species *Aureobasidium pullulans* IFO 4464 was inoculated and continuously cultivated in a nutrient culture medium consisting of the same components as in Table 1 except that "MALTORUP®", a high maltose content starch syrup commercialized by Hayashibara Shoji, Inc., Okayama, Japan, was used as a saccharide at a concentration of 11, 12, 13, 14, 15, 16 or 18 w/v %. The continuous culture was carried out at 27° C. and a pH of 2.4, 2.5, 2.6 or 2.8 for 2 months while replacing a part of the nutrient culture medium with a supplemental nutrient-culture-medium at a dilution rate of $0.01–0.02h^{-1}$ to control the viscosity of the nutrient culture medium to a level below 30 cp. Similarly as in Example A-1, the resultant nutrient culture media were recovered, and in usual manner membrane-filtered and concentrated to obtain high pullulan content products in the form of powder.

The analytical results were as shown in Table 7.

TABLE 7

| No. | Concentration of saccharide (w/v %) | pH | Pullulan content (%, d.s.b) | Average molecular weight (×10,000) |
|---|---|---|---|---|
| 1 | 11 | 2.4 | 84.2 | 22 |
| 2 | 12 | 2.5 | 84.0 | 20 |
| 3 | 13 | 2.6 | 83.6 | 10 |
| 4 | 14 | 2.4 | 74.4 | 22 |

TABLE 7-continued

| No. | Concentration of saccharide (w/v %) | pH | Pullulan content (%, d.s.b) | Average molecular weight (×10,000) |
|---|---|---|---|---|
| 5 | 15 | 2.5 | 72.9 | 20 |
| 6 | 16 | 2.6 | 71.7 | 10 |
| 7 | 18 | 2.8 | 70.5 | 5 |

The products can be advantageously used in a viscosity-imparting agent, coating agent, adhesive, formed product, food product, chemical, pharmaceutical and material for agriculture, forestry, fishery and paper processings, as well as for mining and manufacturing industries.

EXAMPLE B-1

Composition for sealing sliding contact section

To 56 parts by weight of glycerine was added 6 parts by weight of a high pullulan content product in the from of powder prepared by the method in Example A-1, and the mixture was heated to 110° C. and dissolved to homogeneity under stirring conditions. The resultant solution was added with 137 parts by weight of "COUPLING SUGAR®", a glycosyl sucrose commercialized by Hayashibara Shoji Co., Ltd., Okayama, Japan, deaerated and mixed while stirring and preventing the evaporation of water.

The composition showed a viscosity of about 300 cp. When the composition was used as a composition for sealing a sliding contact section of an aerosol container wherein a gas, particularly, a liquefied gas was used as a propellant gas, the composition showed a satisfiable gas-barrier ability even after a 6-month standing of 45° C. or one-year standing of −5° C.

The composition is a non-toxic and safe composition, and this renders it advantageously useful in a variety of compositions for sealing a sliding contact section of an aerosol container in which food products, cosmetics, pharmaceuticals and a variety of products for home use are injected, wherein said sliding contact section contacts with a gas or a liquefied gas having a different pressure from that of the content in the container.

EXAMPLE B-2

Pickled radish (shin-zuke)

Thirty kg of radish was in usual manner pickled, and successively pickled with 10 g saccharin and a mixture consisting of 1.7 kg bran, 10 g saccharin, 30 g glycine, 200 g sodium glutamate, 70 g mixed seasoning, 500 g sorbitol, 360 g salt, 250 ml shochu (low-class distilled spirits) of 70 proof, and 340 g of a high pullulan content product in the form of powder prepared by the method in Example A-2.

The viscosity of the product did not substantially decrease even at 12th day after the processing, and the bran well adhered to the product to exert a satisfiable gloss and texture.

EXAMPLE B-3

Cold insulator

Sixteen parts by weight of a high pullulan content product in the form of powder prepared by the method in Example A-1 was dissolved by heating in 16 parts by weight of glycerine and 68 parts by weight of water, and the resultant solution was added with an adequate amount of an antiseptic and packed to obtain a cold insulator.

When cooled, the product exerts a relatively-high cooling effect, and because of this it can be advantageously used for cooling the head when you are in fever, as well as for retaining the freshness of vegetables.

EXAMPLE B-4

Coating film

A high pullulan content product in the form of liquid prepared by the method in No.4 of Example A-3 was prepared into a 1.0 w/w % aqueous solution, and a fresh egg within 10 hours after the egg-laying was soaked in the aqueous solution for 30 seconds, and dried at 30° C for 2 hours to form a coating film on the egg-shell.

The egg thus obtained was stored at an ambient temperature of 15°–25° C, and the shelf-life was compared with that of an untreated egg as a control. As a result, the shelf-life of the egg with the coating film was 5–10-times longer than that of the control.

EXAMPLE B-5

Packing material for extraction

Commercially available small tea-bag of tea made of a relatively-coarse paper filter was coated by the calender method with a 10 w/w % aqueous solution prepared by dissolving in water a high pullulan content product in the form of liquid prepared by the method in No.6 of Example A-3, and dried with a 60° C. hot-air.

The resultant small tea-bag was injected with an adequate amount of tea for an individual cup of tea and heat sealed. As a control, commercially available tea-bag containing a tea of the same quality as used above. The tea bags were stored at a relative humidity of 60% and 30° C. for one month, and placed in containers and poured with a boiling water to extract the teas, followed by comparing the quality of the tea bags based on the quality of the extracts.

The tea in the tea bag coated with the present high pullulan content product was readily extracted similarly as the control. Both extracts were transparent. The extract prepared with the tea bag coated with the present high pullulan content product was, however, superior to the control in the flavor, color and taste.

EXAMPLE B-6

Paste for binding corrugated paper

A high pullulan content product in the form of liquid prepared by the method in No.3 of Example A-3 was prepared into a 3 w/w % aqueous solution, and 100 parts by weight of which was added with 10 parts by weight of 10 w/v % sodium hydroxide. The mixture was stirred for 20 minutes to obtain a carrier part. Forty parts by weight of corn starch was dissolved in 100 parts by weight of water to obtain a slurry which was then added with one part by weight of borax to obtain a main part. The carrier part was gradually added to the main part, and the mixture was stirred for 5 minutes into a paste.

The viscosity change of the product was lesser than those of conventional starch pastes. The product and conventional starch paste were subjected to an experiment wherein a 240 g/m$^2$ B-type liner and a 125 g/m$^2$ semicenter were pasted together. As a result, conventional starch paste showed a tendency to cause troubles over a speed of 120 m/min, while the present product exhibited a satisfiable binding capacity without causing any trouble even at a speed of 160 m/min.

EXAMPLE B-7

Solid adhesive

A mixture consisting of 30 parts by weight of dimethylsulfoxide, 25 parts by weight of water, 5 parts by weight of elusinan, 5 parts by weight of a high pullulan content product in the form of powder prepared by the method in Example A-2, and 2 parts by weight of dibenzylidene xylitol was dissolved by stirring at 90° C. for one hour. The resultant solution was injected into a lipstick-type cylindrical container, 1 4 mm in diameter and 50 mm in height, having a mechanism capable of lifting up and down the content, and cooled to obtain a solid adhesive.

The product was uniformly spreadable over a craft paper when applied thereon, and sufficient in the initial binding capacity.

The solidity was less influenced by the change of an ambient temperature, and this exerted a satisfiable spreadability and binding capacity.

EXAMPLE B-8

Film

A high pullulan content product in the form of liquid prepared by the method in No.4 of Example A-3 was prepared into a 15 w/w % aqueous solution, and one w/w %, d.s.b., of carragheenan and 0.1 w/w %, d.s.b., of sucrose monolaurate were dissolved in the aqueous solution. The resultant solution was poured on a polyester film and conveyed at a speed of 3 m/min to form a film 0.03 mm thick which was then dried with a 90° C. hot-air to obtain the captioned product.

Unlike a film consisting of pullulan, the product is an edible film which does not readily dissolve in an aqueous system but gradually dissolves and disintegrates in the system.

Accordingly, similar to a medicinal wafer, the product can be advantageously used as an agent for wrapping an unswallowable powdery medicine, as well as a film for fixing an artificial tooth, because the product exhibits a satisfiable viscosity when dissolved and disintegrated.

EXAMPLE B-9

Fiber

A high pullulan content product in the form of liquid prepared by the method in No.1 of Example A-3 was prepared into a 40 w/w % solution, and in which alginic acid was dissolved to give a concentration of 2 w/w %, d.s.b. The resultant solution as a material solution for spinning was heated to 60° C., and pressed out in the air of an ambient temperature at a pressure of 3 kg/cm$^2$ from a cylindrical nozzle having a diameter of 0.3 mm and a length of 1 mm to form a strand which was then rolled up with a winder while evaporating water to effect drying.

The product having a satisfiable strength was about 20 μm thick. The product can be twisted, knitted and woven, and has a readily water-solubility without a fear of causing toxicity and skin stimulation, and these render it suitably used in an absorbent cotton, sanitary napkin, gauze and thread for operation.

When mixed with other fibers, the product can be used as a material for underwear or other clothing because it has a satisfiable hygroscopicity, non electrification and stainability.

EXAMPLE B-10

Paper

A mixture was prepared by mixing a fiber prepared by the method in Example B-9 which had been cut into 5–10 cm and a wood pulp in a half amount of the fiber, which was then suspended to homogeneity in about 50-fold volumes of 75 v/v % methanol (10° C.), and subjected to a paper machine.

The resultant product was dried while regulating the temperature of a drying roll at 50°–80° C., and passed through a calender roll for a relatively-short period of time to obtain a paper.

The product thus obtained has a smooth surface and a relatively-low level of gloss like a Japanese paper. The product well harmonized with an ink for writing without blotting.

The product readily dissolves in hot-water, and this renders it advantageously useful in a special use such as confidential documents.

The product is edible so that it is suitably used as a material for enclosing a pharmaceutical and a packing material for food products such as a seasoning, coffee and cocoa.

EXAMPLE B-11

Expanded sheet

One hundred parts by weight of polyvinylchloride was added with 60 parts by weight of dioctyl phthalate as a plasticizer, and the resultant mixture was further added with a 50 w/w % aqueous solution of a high pullulan content product in the form of powder, prepared by the method in Example A-2, in an amount of which gave a concentration of 30 w/w %, d.s.b., against the total weight. The mixture was kneaded to homogeneity by a mixer and poured onto an aluminum plate by using an applicator to form a sheet 3 mm thick which was then heated by an air-heating furnace at 190° C. for 10 minutes to obtain an expanded sheet consisting of uniform cells having an about 5-fold expansion coefficient.

The product is suitably used as a sound-insulating material, heat-insulating material, crating material, and shock-absorbing material. The product was disintegrated within one month when allowed to soak in a river, while an expanded sheet which had not been added with the product still remained its original shape even after 12 months.

EXAMPLE B-12

Tee

A mixture consisting of 10 parts by weight of a high pullulan content product in the form of powder prepared by the method in Example A-2, and 4 parts by weight of Japanese acid clay was sprayed with water to give a moisture content of about 30 w/w % under stirring conditions, and the resultant mixture was formed at 120° C. into a tee by an injection molding machine, soaked in a solution of shellac and alcohol, and air-dried to obtain the captioned product.

The product is broken into small masses at a shot, gradually disintegrated by rainwater, and biodegraded.

Thus, the product does not spoil the view of a golf course and disrupt the environment.

EXAMPLE B-13

Flowerpot

A mixture consisting of 100 parts by weight of a high pullulan content product in the form of powder prepared by the method in Example A-1, and 15 parts by weight of glycerine was formed by an injection molding machine at 135° C. into a flowerpot which was then soaked in a dissolved wax, and cooled at an ambient temperature to obtain the captioned product.

The product is gradually disintegrable and biodegradable, and these render it advantageously useful as a flowerpot for transplantation. Plants grown in the product can be planted out without removing them therefrom so as not to be damaged.

EXAMPLE B-14

Capsule

Forty parts by weight of a high pullulan content product in the from of powder prepared by the method in Example A-1, 60 parts by weight of gelatin, and 30 parts by weight of glycerine were mixed, and the resultant mixture was added with 80 parts by weight of water, dissolved by heating at about 70° C., and deaerated to obtain a coating solution which was then in usual manner used for encapsulating a high vitamin-E content oil to obtain a soft capsule.

Unlike a capsule consisting of gelatin, the product has properties such as a relatively-high gas-barrier ability, readily solubility in an aqueous system, and ability to stabilize vitamin E.

EXAMPLE B-15

Fertilizer in the form of rod

Seventy parts by weight of a compound fertilizer comprising 14 w/w % N, 8 w/w % $P_2O_5$ and 12 w/w % $K_2O$, 10 parts by weight of a high pullulan content product in the form of powder prepared by the method in Example A-1, 15 parts by weight of calcium sulfate, and 5 parts by weight of water were mixed to homogeneity, and the resultant mixture was heated to 80° C. by an extruder, having an L/D ratio of 20, pressure ratio of 1.8 and die diameter of 30 mm, to obtain the captioned product.

In use the product does not require a vessel, and it has a readily handleability and satisfiable strength for a total layer application. The elution speed of the ingredients contained in the product is controllable by changing their compounding ratio. If necessary, the product can be readily added with a plant hormone, agricultural chemical and soil conditioner.

EXAMPLE B-16

Formed tobacco product

To 50 parts by weight of a powdered tobacco material prepared from a bright-yellow tobacco plant was added 200 parts by weight of a 2 w/w % aqueous solution of a high pullulan content product in the form of powder prepared by the method in Example A-2, and 0.1 part by weight of lactitol, and the resultant mixture was extruded from a slit of 0.2 mm onto an endless stainless-steel belt, and dried by infrared to obtain 65 parts by weight of a tobacco in the form of sheet having a moisture content of 13 w/w %.

The product is suitable as a tobacco or filler for cigarettes, and a binder for cigars and cigarillos. The product inhibits the deterioration of the ingredients of tobaccos, and has a relatively-high perfume-retaining ability without a fear of forming unsatisfiable smell and taste when smoked, and because of these you can enjoy a satisfiable flavor and taste. The content of nicotine and the burning speed are controllable by changing the compounding ratio of pullulan in the product.

EXAMPLE B-17

Sour milk beverage to promote the growth of Bifidobacterium

Ten thousand of defatted milk was sterilized at 80° C. for 20 minutes, cooled to 40° C., and added with 300 parts by weight of a seed culture of a lactic bacterium as a starter. The mixture was subjected to fermentation at a temperature of 35°–37° C. for 10 hours. Thereafter, the mixture was homogenized and added with 4,000 parts by weight of an isomerized-sugar syrup, 2,000 parts by weight of sucrose, and 170 parts by weight of a high pullulan content product in the form of powder prepared by the method in Example A-1. The resultant mixture was mixed by stirring, sterilized while keeping it at 70° C., cooled, added with a small amount of a flavor, and bottled to obtain a sour milk beverage to promote the growth of microorganisms of Bifidobacterium like conventional lactic acid beverage.

The product exerts an effect of promoting the growth of microorganisms of Bifidobacterium and an effect as a dietary fiber, and because of these it lowers the intestinal pH-level, inhibits the growth of putrefactive bacteria, and prevents constipation.

EXAMPLE B-18

Low-caloric bakery

Six parts by weight of a strong flour and 12 parts by weight of amylose as a part of a main material were added with water, and the mixture was kneaded with a mixer. The resultant mixture was added with 21.4 parts by weight of a supplemental material consisting of 6 parts by weight of margarine, 2.5 parts by weight of sucrose, 6 parts by weight of egg, 0.4 parts by weight of salt and 6.5 parts by weight of water; and further added with 5.2 parts by weight of a fermentation material consisting of 0.8 parts by weight of dry yeast, 0.4 parts by weight of sucrose and 4 parts by weight of water. Thus, a dough having a satisfiable solidity was obtained. The dough was subjected to a first fermentation of 30° C. for 60 minutes while removing a formed gas. Thereafter, the resultant dough was added as the rest part of the main material with 3 parts by weight of a strong flour and 9 parts by weight of a high pullulan content product in the form of powder prepared by the method in Example A-2, and the mixture was kneaded to homogeneity while controlling the solidity by the addition of a prescribed amount of water. The dough thus obtained was allowed to stand in a refrigerator for 60 minutes to effect a second fermentation, then subjected to a third fermentation of 35° C. for 30 minutes while removing a formed gas, and formed. The resultant dough was subjected to a fourth fermentation of 35° C. for 30 minutes, placed in an oven kept at 210° C., and baked for 20 minutes. As a control, a bakery was prepared similarly as above excepting 30 parts by weight of a strong flour as the main material and 8 parts by weight water as the supplemental material were used.

As referred to the appearance, the product was slightly darker than the control, and, as referred to the internal appearance, the internal texture of the product was satisfiably uniform. The taste of the product was substantially the same as that of the control, and panels answered that the product was free from unsatisfiable taste and smell, as well as being relatively plane. The panels did not feel an unsatisfiable feeling such as an adhesion to the teeth, and answered that the product had a satisfiable biting-property and a slight solidity of the surface.

The product exerts a growth-promoting effect on microorganisms of Bifidobacterium and a satisfiable effect as a low-caloric food and dietary fiber, and because of these it can be advantageously used in the maintenance and promotion of health and beauty.

EXAMPLE B-19

Dentifrice

Forty-five parts by weight of calcium secondary phosphate, 30.0 parts by weight of a 10 w/w % aqueous solution prepared with a high pullulan content product in the form of liquid obtained by the method in No.4 of Example A-3, 30.0 parts by weight of polyethylene glycol having an average molecular weight of 1,500, 1.5 parts by weight of sodium lauryl sulfate, 17.0 parts by weight of glycerine, 0.5 parts by weight of polyoxyethylene sorbitane monolaurate, 0.2 parts by weight of "αG sweet", a sweetener of α-glycosyl stevioside commercialized by Toyo Sugar Refining Co., Ltd., Tokyo, Japan, and 0.05 parts by weight of an antiseptic were mixed in usual manner to prepare the captioned product.

The product having a moderate sweetness is suitably used as a dentifrice for children. The product contains an association complex of pullulan and polyethylene glycol, and because of this it is a readily usable dentifrice free of glutinousness and stickiness in comparison with a dentifrice containing pullulan but not an association complex.

EXAMPLE B-20

Cosmetic pack

A cosmetic pack was in usual manner prepared by mixing to homogeneity 0.5 parts by weight of linolenic acid with 1.5 parts by weight of squalene, 0.5 parts by weight of polyoxyethylene hydrogenated castor oil, 5.5 parts by weight of sodium L-lactate, 4.0 parts by weight of glycerine, 50.0 parts by weight of a 40 w/w % aqueous solution prepared with a high pullulan content product in the form of liquid obtained by the method in No.2 of Example A-3, 10.0 parts by weight of ethanol, and 33.0 parts by weight of purified water to obtain the captioned product.

The product is suitably used as a skin-whitening agent and advantageously used in the treatment and prevention of local and systemic pigmentation such as chloasma, freckle, sunburn and adisonism.

EXAMPLE B-21

Shampoo

Eighty parts by weight of a 2.5 w/w % aqueous solution of a high pullulan content product in the form of liquid obtained by the method in No.4 of Example A-3 was added with 13.0 parts by weight of ethanol, 2.0 parts by weight of glycerine, 0.3 parts by weight of a flavor, and 1.5 parts by weight of polyoxyethyle sorbitane monolaurate, and the mixture was dissolved by mixing to obtain a shampoo.

When you shampoo with the product, you can readily pass your fingers through your hair, and you are satisfied with a soft-touching of your hair. Thus, the product is a satisfiable shampoo excellent in an actual usability and feeling.

EXAMPLE B-22

Sugar-coated tablet

A crude tablet 150 mg weight was coated until it gives the total weight of about 230 mg with a first coating solution consisting of 40 parts by weight of crystalline maltitol, 20 parts by weight of a 10 w/w % aqueous solution prepared with a high pullulan content product in the form of liquid obtained by the method in No.2 of Example A-3, 12 parts by weight of water, 25 parts by weight of talc, and 3 parts by weight of titanium oxide. The resultant tablet was coated with a second coating solution consisting of 25 parts by weight of water, 65 parts by weight of a fresh preparation of the same crystalline maltitol, and 10 parts by weight of a fresh 10 w/w % aqueous solution prepared with the same high pullulan content product, and further coated with a wax solution to obtain a sugar-coated tablet having a satisfiable glossy appearance.

The sugar-coating step of the product is readily conducted, and the product has a satisfiable shock-tolerance and retains a relatively-high quality for a relatively-long period of time.

EXAMPLE B-23

Plasma expander

A high pullulan content product in the from of liquid prepared by the method in No.7 of Example A-3 was prepared into a 10 w/w % aqueous solution which was then added with methanol to give a concentration of 40 v/v %. The lower-part layer of the resultant mixture solution was removed, and the resultant upper-part layer was added with methanol to give a concentration of 55 v/v % and allowed to stand, and the lower part of a layer was separated and recovered. The methanol in the resultant lower part was distilled, and the resultant pullulan solution was decolored by the addition of an activated charcoal, desalted with ion-exchange resins ($H^+$- and $OH^-$-form), and filtered with a membrane filter. The resultant purified pullulan was concentrated, dried and pulverized to obtain a pyrogen-free white pullulan powder having an average molecular weight ($\overline{Mw}$) of 50,000 and a ratio of the average molecular weight against the average molecular-number $\overline{Mw}/\overline{MN}$ ratio) of 1.4 in the yield of about 45%. The pullulan thus obtained was prepared into an about 4–10 w/v % aqueous solution which was then added with an isotonicity-imparting agent such as salts and saccharides, and sterilized to obtain an injection.

The product is suitably used as a plasma expander and bloodstream-improving agent.

As described above, the present inventors found that pullulan is prepared in a higher pullulan-productivity than conventional preparations by continuously cultivating a microorganism capable of producing pullulan in a nutrient culture medium containing a 10–20 w/v % saccharide while controlling the viscosity to a level below 30 cp, and established an industrially-useful high pullulan content product wherein the molecular weight of said pullulan is less than 250,000, as well as its preparation and uses.

The present invention provides a high pullulan content product by using a continuous culture in a relatively-large scale and low-production cost, and widens the applicability of pullulan in a variety of fields such as a viscosity-imparting agent, coating agent, adhesive, formed product, food product, cosmetic, pharmaceutical, and material for agriculture, forestry, stock raising and paper processings, as well as for mining and manufacturing industries.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for preparing a pullulan product by continuous culture, which comprises the steps of:
   (a) cultivating a microorganism capable of producing pullulan at a pH exceeding 2.0 but not higher than 4.0 in a nutrient culture medium containing 10–20 w/v % of a saccharide to produce and accumulate pullulan in said nutrient culture medium while controlling the viscosity of said nutrient culture medium to a level below 30 centipoise; and
   (b) purifying and recovering a product which contains pullulan.

2. The process of claim 1, wherein the product obtained in step (b) contains at least about 50 w/w % of pullulan, on a dry solid basis.

3. The process of claim 1, wherein said saccharide is one or more members selected from the group consisting of glucose, fructose, sucrose, maltose, maltooligosaccharides, isomaltooligosaccharides, saccharified starch, invert sugars, isomerized sugars and molasses.

4. The process of claim 1, wherein said cultivating step is effected under aerobic conditions.

5. The process of claim 1, wherein said cultivating step is effected in the presence of an amylase which partially hydrolyzes pullulan.

6. The product of claim 5, wherein said amylase is a member selected from the group consisting of a liquefying α-amylase and isoamylase.

7. The process according to claim 1, wherein the viscosity is controlled by replacing a portion of said nutrient culture medium with a supplemental nutrient culture medium.

8. The process according to claim 1, wherein the viscosity is controlled by adding a sufficient amount of an amylase to said nutrient culture medium to partially hydrolyze the pullulan produced and accumulated in step (a) and lower the viscosity of said nutrient culture medium.

9. The process according to claim 1, wherein the microorganism is of the genus Aureobasidium.

10. The process according to claim 9, wherein the microorganism is selected from *Aureobasidium fermentans* and *Aureobasidium pullulans*.

11. The process according to claim 1, wherein the pullulan produced has an average molecular weight less than 250,000.

12. The process according to claim 11, wherein the pullulan produced has an average molecular weight in the range of between about 40,000 and 250,000.

* * * * *